(12) United States Patent
Herlihy et al.

(10) Patent No.: US 8,785,515 B2
(45) Date of Patent: Jul. 22, 2014

(54) SENSITIZER FOR CATIONIC PHOTOINITIATORS

(75) Inventors: Shaun Lawrence Herlihy, Kent (GB); Robert Stephen Davidson, Leicester (GB)

(73) Assignee: Sun Chemical Corporation, Parsippany, NJ (US)

( * ) Notice: Subject to any disclaimer, the term of this patent is extended or adjusted under 35 U.S.C. 154(b) by 1051 days.

(21) Appl. No.: 12/598,113

(22) PCT Filed: May 9, 2008

(86) PCT No.: PCT/IB2008/001187
§ 371 (c)(1),
(2), (4) Date: Oct. 29, 2009

(87) PCT Pub. No.: WO2008/139315
PCT Pub. Date: Nov. 20, 2008

(65) Prior Publication Data
US 2010/0129563 A1 May 27, 2010

(30) Foreign Application Priority Data

May 11, 2007 (GB) .................................. 0709119.2

(51) Int. Cl.
*C08F 2/50* (2006.01)
*C08J 3/28* (2006.01)
*C08J 7/18* (2006.01)

(52) U.S. Cl.
USPC ........ 522/30; 522/7; 522/15; 522/31; 522/67; 522/68; 522/25; 522/26; 522/48; 522/63; 522/168; 522/163; 522/183; 522/178; 522/169; 522/904; 427/508; 427/511; 427/516; 427/517; 427/520

(58) Field of Classification Search
USPC ............. 522/168, 170, 25, 26, 30, 31, 48, 63, 522/67, 68, 163, 178, 169, 904, 183, 7, 15; 427/508, 511, 516, 517, 520
See application file for complete search history.

(56) References Cited

U.S. PATENT DOCUMENTS

| | | | |
|---|---|---|---|
| 3,042,679 | A | 7/1962 | Clark |
| 3,168,525 | A | 2/1965 | Baizer |
| 3,184,503 | A | 5/1965 | Baizer |
| 4,997,717 | A | 3/1991 | Rembold et al. |
| 5,326,885 | A | 7/1994 | Olivero et al. |
| 6,313,188 | B1 | 11/2001 | Takahashi |
| 6,593,388 | B2 | 7/2003 | Crivello |

FOREIGN PATENT DOCUMENTS

| | | |
|---|---|---|
| EP | 0927726 A1 | 7/1999 |
| GB | 1107845 A | 3/1968 |
| JP | 10045743 A | 2/1998 |
| JP | 2006-208607 A | 8/2006 |
| WO | WO-9322451 A1 | 11/1993 |
| WO | WO03007491 | 1/2003 |
| WO | WO-03072567 A1 | 9/2003 |
| WO | WO-03072568 A1 | 9/2003 |
| WO | WO-2004055000 A1 | 7/2004 |
| WO | WO-2006073021 A1 | 7/2006 |
| WO | WO-2006-098676 A1 | 9/2006 |
| WO | WO-2006093678 A2 | 9/2006 |

OTHER PUBLICATIONS

Al-Azemi et al., Polymer, vol. 43, pp. 2161-2167 (2002).
Kawasaki et al., Tetrahedron, vol. 53, No. 18, pp. 6337-6350 (1997).
Office Action dated Apr. 30, 2013 for JP Application No. 2010-507021.

*Primary Examiner* — Sanza McClendon
(74) *Attorney, Agent, or Firm* — Frost Brown Todd LLC

(57) ABSTRACT

Polycyclic aromatic compounds of formula (I) having at least two conjugated aromatic rings at least one of which has a substituent comprising a cyclic carbonate group can be used as sensitizers for cationic photoinitiators, especially iodonium compounds, and may also function as monomers in cationically initiated radiation curable compositions, especially coating compositions, such as printing inks and varnishes.

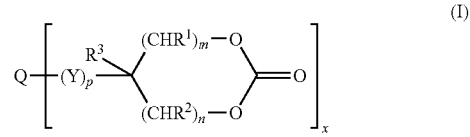

20 Claims, No Drawings

SENSITIZER FOR CATIONIC PHOTOINITIATORS

The present invention relates to a series of new compounds which may be used as sensitisers for cationic photoinitiators, especially iodonium compounds, or as monomers for use in compositions, especially coating compositions, such as printing inks or varnishes, which are energy-curable, e.g. UV curable, via a cationic mechanism.

Polycyclic aromatic compounds, such as anthracene, naphthalene and derivatives thereof, have long been known for use as sensitisers of iodonium photoinitiators in the cationic ring-opening polymerisation of epoxides (see, for example, U.S. Pat. No. 6,313,188, EP 0927726, WO 2006/073021, U.S. Pat. No. 4,997,717, U.S. Pat. No. 6,593,388, and WO 03/076491). However, by their very nature, these compounds do not participate in the polymerisation reaction and so are left unreacted in the end product. This is generally considered undesirable, since they can migrate to the surface, contaminate materials in contact with the polymer and so on.

In our copending PCT application No. WO 2006/093678, we disclose that certain polyfunctional cyclic carbonates, i.e. compounds having two or more cyclic carbonate groups which are capable of participation in a ring-opening polymerisation process, can be used as monomers in such compositions, and that this leads to excellent cure of the resulting compositions.

WO 93/22451 describes the synthesis of enantiomerically pure beta-blocker precursor compounds based on cyclic carbonate structures containing a naphthalene functionality.

GB 1107845 describes derivatives of dihydronaphthalene containing cyclic carbonate groups that are useful as pest control substances.

U.S. Pat. No. 3,184,503, U.S. Pat. No. 3,168,525 and U.S. Pat. No. 3,042,679 describe the synthesis of a 5-substituted oxazolidones as useful intermediates in the synthesis of amino alcohols and their corresponding beta-halo amines or carbamates. Oxazolidone substituents may include aromatic compounds such as naphthalene.

JP 100045743 describes the synthesis of calixarene compounds containing multiple cyclic carbonate groups.

We have now discovered that the incorporation of cyclic carbonate groups as substituents on polycyclic aromatic compounds results in a series of new compounds which not only act as sensitisers for cationic photoinitiators, especially iodonium compounds, but also participate in the polymerisation reaction and so end up chemically incorporated into the resulting polymer.

Thus, the present invention consists in a polycyclic aromatic compound having at least two conjugated aromatic rings at least one of which has a substituent comprising a cyclic carbonate group.

The invention further provides a composition comprising a cationic photoinitiator, especially an iodonium compound, and a polycyclic aromatic compound having at least two conjugated aromatic rings at least one of which has a substituent comprising a cyclic carbonate group.

The invention still further provides a cationically curable composition comprising a cationic photoinitiator, especially an iodonium compound, a polycyclic aromatic compound having at least two conjugated aromatic rings at least one of which has a substituent comprising a cyclic carbonate group and a cationically polymerisable monomer or oligomer.

A preferred class of polyfunctional cyclic carbonate compounds for use in the present invention comprises those compounds of formula (I):

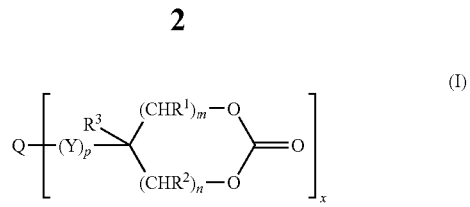

in which:

Q represents a residue of a polycyclic aromatic compound having at least two conjugated aromatic rings and having a valency x;

Y is an aliphatic carbon chain which may be interrupted by one or more oxygen atoms, sulphur atoms, phenylene groups, carbonyl groups, epoxide groups or linear or cyclic carbonate groups;

p is 0 or 1;

$R^1$ and $R^2$ are the same as or different from each other, and each represents a hydrogen atom, an alkyl group, a hydroxyalkyl group, an alkoxyalkyl group, an alkoxycarbonylalkyl group or a $C_2$-$C_5$ carbon chain which is attached to a carbon atom of Y to form a fused ring;

$R^3$ represents a hydrogen atom or an alkyl group; and m and n are the same as or different from each other, and each is zero or a number from 1 to 4, provided that (m+n) is zero or a number from 1 to 4.

In these compounds of formula (I), Q is a residue of a polycyclic, and preferably polyvalent, aromatic compound having a valency x, which is preferably from 2 to 4. Examples of such compounds of which the residues may be represented by Q include biphenyl, anthracene, naphthalene, pentalene, indene, azulene, heptalene, biphenylene, indacene, acenaphthylene, fluorene, phenalene, phenanthrene, fluoranthrene, acephenanthrylene, triphenylene, pyrene, chrysene, naphthacene, pleiadene, picene, perylene, pentaphene, pentacene, tetraphenylene, hexaphene, hexacene, rubicene, coronene, trinaphthylene, heptaphene, heptacene, pyranthrene and ovalene. Of these, naphthalene and anthracene are preferred.

The aromatic rings of the compound Q may be fused rings or they may be simply linked by one or more bonds, provided that the aromaticity extends over the plurality of aromatic rings. The number, x, of cyclic carbonate groups is preferably 2.

The groups represented by Q may be unsubstituted other than by the carbonate-containing groups or they may be substituted by further and different substituents. Other than those substituents well known in the art to interfere with cationic polymerisation, there is no particular restriction on the nature of such substituents. Examples include alkyl groups, such as those exemplified below in relation to $R^1$ etc., alkoxy groups, such as the methoxy, ethoxy, propoxy or butoxy groups, and fatty acid groups, such as the carboxymethyl, carboxyethyl, carboxypropyl or carboxybutyl groups or such groups which have been esterified.

Where Y is present, it is an aliphatic carbon chain which may be interrupted by one or more oxygen atoms, sulphur atoms, phenylene groups, carbonyl groups, epoxide groups or linear or cyclic carbonate groups. It preferably has from 1 to 20 atoms in its aliphatic chain.

Of these compounds, we prefer those compounds having the formula (Ia):

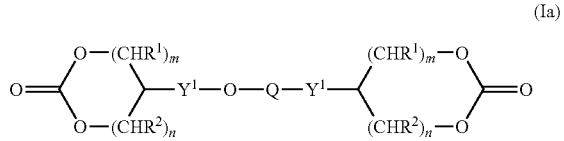

(Ia)

in which $R^1$, $R^2$, n, m and Q are as defined above and $Y^1$ represents an aliphatic group having from 1 to 3 carbon atoms, preferably an alkylene group having from 1 to 3 carbon atoms. More preferably $Y^1$ represents a methylene group.

A particularly preferred class of compounds of the present invention are those compounds of formula (I) or (Ia) in which: Q represents a residue of an anthracene or naphthalene ring system, which is unsubstituted or has at least one alkyl (e.g. $C_1$-$C_4$ alkyl, especially ethyl) substituent; m+n=1; $R^1$, $R^2$ and $R^3$ [formula (I)] all represent hydrogen atoms; Y [formula (I)] is $Y^1$—O—; and $Y^1$ represents an alkylene group having from 1 to 3 carbon atoms, more preferably a methylene group.

In the compounds of formulae (I) and (II), where $R^1$, $R^2$, $R^3$ or $R^4$ represents an alkyl group, this may be a straight or branched chain group having from 1 to 20, more preferably from 1 to 10, still more preferably from 1 to 6 and most preferably from 1 to 3, carbon atoms, and examples of such groups include the methyl, ethyl, propyl, isopropyl, butyl, isobutyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl, isohexyl, heptyl, octyl, nonyl, decyl, dodecyl, tridecyl, pentadecyl, octadecyl, nonadecyl and icosyl groups, but preferably the methyl, ethyl, propyl and t-butyl groups, and most preferably the methyl or ethyl group.

Where $R^1$, $R^2$, $R^3$ or $R^4$ represents a hydroxyalkyl group, this may be a straight or branched chain group having from 1 to 6, preferably from 1 to 4, carbon atoms, and examples include the hydroxymethyl, 1- or 2-hydroxyethyl, 1-, 2- or 3-hydroxypropyl, 1- or 2-hydroxy-2-methylethyl, 1-, 2-, 3- or 4-hydroxybutyl, 1-, 2-, 3-, 4- or 5-hydroxypentyl or 1-, 2-, 3-, 4-, 5- or 6-hydroxyhexyl groups. Of these, we prefer those hydroxyalkyl groups having from 1 to 4 carbon atoms, preferably the hydroxymethyl, 2-hydroxyethyl, 3-hydroxypropyl and 4-hydroxybutyl groups, and most preferably the hydroxymethyl group.

Where $R^1$, $R^2$, $R^3$ or $R^4$ represents an alkoxyalkyl group, the alkoxy and alkyl parts both preferably have from 1 to 6 carbon atoms, and examples include the methoxymethyl, ethoxymethyl, propoxymethyl, isopropoxymethyl, butoxymethyl, 2-methoxyethyl, 3-methoxypropyl, 2-methoxypropyl and 4-ethoxybutyl groups.

Where $R^1$, $R^2$, $R^3$ or $R^4$ represents an alkoxycarbonylalkyl group, the alkoxy and alkyl parts both preferably have from 1 to 6 carbon atoms, and examples include the methoxycarbonylmethyl, ethoxycarbonylmethyl, propoxycarbonylmethyl, isopropoxycarbonylmethyl, butoxycarbonylmethyl, 2-methoxycarbonylethyl, 3-methoxycarbonylpropyl, 2-methoxycarbonylpropyl and 4-ethoxycarbonylbutyl groups.

In formula (I), where $R^1$ or $R^2$ represents a carbon chain forming, with a carbon atom of Y a fused ring, this has from 2 to 5 carbon atoms and may be, for example, a dimethylene, trimethylene, tetramethylene or pentamethylene group.

Examples of preferred polyfunctional cyclic carbonates for use in the present invention include compounds of formulae:

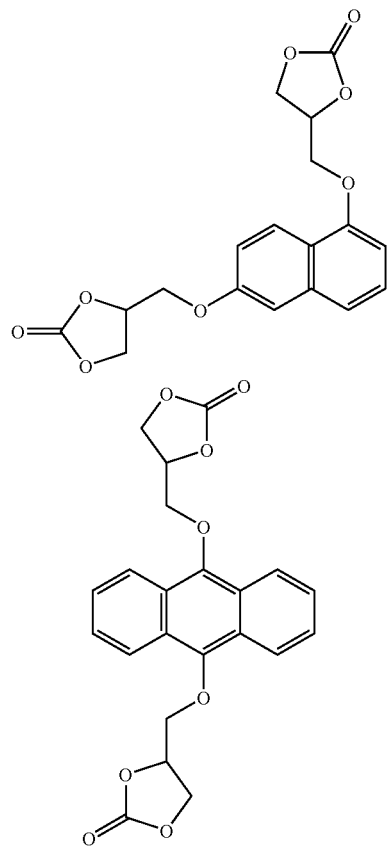

Where the polycyclic aromatic carbonate compound is to be used simply as a sensitiser, we prefer that it should comprise from 0.5 to 3% by weight of the total composition, although the exact amount may vary widely, depending on the photoinitiator and the other reagents. Where the polycyclic aromatic carbonate compound is to be a monomer component, there is no particular limit on the amount used, although, since such compounds will not normally homopolymerise, it is preferred that they should not be the sole monomeric component and, in general, should be no more than 50% of the polymerisable components. In this case, the amount used is preferably from 1 to 50% by weight, more preferably from 10 to 30% by weight, and most preferably from 15 to 25% by weight, of the total polymerisable components of the composition.

5-Membered cyclic carbonates are easily prepared on an industrial scale, for example by carbon dioxide insertion into epoxide groups or other known methods.

Preferred copolymerisable monomers or oligomers for use in the compositions of the present invention include epoxides, oxetanes, and sulphur analogues thereof, in particular epoxides and/or oxetanes, of which the cycloaliphatic epoxides are preferred.

Typical epoxides which may be used include the cycloaliphatic epoxides (such as those sold under the designations Cyracure UVR6105, UVR6107, UVR6110 and Uvacure 1500 from Cytec), and cycloaliphatic epoxy silicone materials such as those marketed by GE Bayer silicones/Momentive, which are well known to those skilled in the art.

Other epoxies which may be used include such epoxy-functional oligomers/monomers as the glycidyl ethers of polyols [bisphenol A, alkyl diols or poly(alkylene oxides), which be di-, tri-, tetra- or hexa-functional]. Also, epoxides derived by the epoxidation of unsaturated materials may also be used (e.g. epoxidised soybean oil, epoxidised polybutadiene or epoxidised alkenes). Naturally occurring epoxides may also be used, including the crop oil collected from *Vernonia galamensis*.

Examples of suitable oxetanes include 3-ethyl-3-hydroxymethyl-oxetane, 3-ethyl-3-[2-ethylhexyloxy)methyl]oxetane, bis[1-ethyl(3-oxetanyl)]methyl ether, bis[1-ethyl(3-oxetanyl)]methyl ether, oxetane functional novolac polymers and methyl silicon trioxetane.

As well as epoxides and optionally oxetanes, other reactive monomers/oligomers which may be used include the vinyl ethers of polyols [such as triethylene glycol divinyl ether, 1,4-cyclohexane dimethanol divinyl ether and the vinyl ethers of poly(alkylene oxides)]. Examples of vinyl ether functional prepolymers include the urethane-based products supplied by Allied Signal. Similarly, monomers/oligomers containing propenyl ether groups may be used in place of the corresponding compounds referred to above containing vinyl ether groups.

Other reactive species can include styrene derivatives and cyclic esters (such as lactones and their derivatives).

The composition of the present invention also contains a cationic photoinitiator. There is no particular restriction on the particular cationic photoinitiator used, and any cationic photoinitiator known in the art may be employed. Examples of such cationic photoinitiators include sulphonium salts (such as the mixture of compounds available under the trade name UVI6992 from Dow Chemical), thianthrenium salts (such as Esacure 1187 available from Lamberti), iodonium salts (such as Omnicat 440 from IGM, Irgacure 250 from Ciba Speciality Chemicals, Rhodorsil 2074 & 2076 from Rhodia and UV 2257 from Deuteron and UV 9380c from General Electric), phenacyl sulphonium salts and the thioxanthonium salts, such as those described in WO 03/072567 A1, WO 03/072568 A1, and WO 2004/055000 A1, the disclosures of which are incorporated herein by reference.

The preferred photoinitiators are the iodonium salts, since the compounds of the present invention can act as sensitisers to these compounds.

The composition of the present invention may be formulated as a printing ink, varnish, adhesive, paint or any other coating composition which is intended to be cured by energy, which may be supplied by irradiation, whether by ultraviolet or electron beam. Such compositions will normally contain at least a polymerisable monomer, prepolymer or oligomer, and a cationic photoinitiator, as well as the cyclic carbonate, but may also include other components well known to those skilled in the art, for example, reactive diluents and, in the case of printing inks and paints, a pigment or dye.

It is also common to include polyols in ultraviolet cationic curable formulations, which promote the cross-linking by a chain-transfer process. Examples of polyols include the ethoxylated/propoxylated derivatives of, for example, trimethylolpropane, pentaerythritol, di-trimethylolpropane, di-pentaerythritol and sorbitan esters, as well as more conventional poly(ethylene oxide)s and poly(propylene oxide)s. Other polyols well known to those skilled in the art are the polycaprolactone diols, triols and tetraols, such as those supplied by Solvay.

Additives which may be used in conjunction with the principal components of the coating formulations of the present invention include stabilisers, plasticisers, pigments, waxes, slip aids, levelling aids, adhesion promoters, surfactants and fillers.

The amounts of the various components of the curable composition of the present invention may vary over a wide range and, in general, are not critical to the present invention. However, we prefer that the amount of the polymerisable components (i.e. the epoxide, oxetane, if used, and other monomers, prepolymers and oligomers, if used) should be from 40 to 90% of the total composition. The epoxide(s) preferably comprise from 30 to 80% of the polymerisable components in the composition of the present invention, and the oxetanes, preferably multi-functional oxetane(s), if used, preferably comprise from 5 to 40% of the polymerisable components in the composition of the present invention. The amount of cationic photoinitiator is normally from 1.0 to 10% by weight, more preferably from 2.0 to 8%, by weight of the entire composition.

Other components of the curable composition may be included in amounts well known to those skilled in the art.

The curable compositions of this invention may be suitable for applications that include various kinds of coatings, including protective, decorative and insulating coatings; release coatings; coil coatings; primers; potting compounds; sealants; adhesives; photoresists; textile coatings; and laminates. The compositions may be applied to a variety of substrates, e.g., metal, rubber, plastic, wood, moulded parts, films, paper, glass cloth, concrete, and ceramic. The curable compositions of this invention are particularly useful as inks for use in a variety of printing processes, including, but not limited to, lithography, flexography, inkjet and gravure. The compositions are especially useful for inkjet printing. Details of such printing processes and of the properties of inks needed for them are well known and may be found, for example, in The Printing Ink Manual, 5$^{th}$ Edition, edited by R. H. Leach et al., published in 1993 by Blueprint, the disclosure of which is incorporated herein by reference. They are also useful as adhesives, release coatings and primers.

In particular, unlike many other ink formulations, it is possible to vary the viscosity of coating compositions of the present invention over a very wide range, from the relatively low viscosities required for flexographic and inkjet processes to the rather higher viscosities required for lithographic inks and varnishes.

Where the compositions of the present invention are used for inks, these typically comprise, as additional components to those referred to above, one or more of pigments, waxes, stabilisers, and flow aids, for example as described in "The Printing Ink Manual".

Thus, the invention also provides a process for preparing a cured coating composition, which comprises applying a composition according to the present invention to a substrate and exposing the coated substrate to curing radiation sufficient to cure the coating.

The invention is further illustrated by the following non-limiting Examples.

EXAMPLE 1

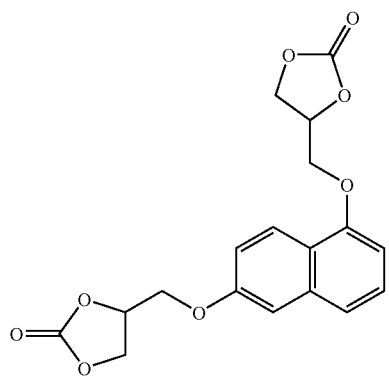 [SMILES: O=C1OCC(COc2ccc3c(OCC4COC(=O)O4)cccc3c2)O1]

50.74 g of naphthalene diglycidyl ether (EPICLON HP-4032D from Dainippon Ink and Chemical Company, Japan), and 0.50 g of tetrabutyl ammonium bromide were mixed in a 0.5 liter Parr pressure reactor with a magnetic stirrer. The reactor was sealed and carbon dioxide gas was pressurised into the reactor to an initial pressure of approximately 350 psi at room temperature. The reactor was then heated to a temperature of approximately 150° C. The temperature/pressure profile was monitored throughout. When the temperature had been held constant at 150° C. and there appeared to be no further change in the pressure, the reactor was cooled and the pressure released. The product was removed from the reactor.

Product yield 58 g of a glassy solid.

The product was analysed by IR and showed a very strong carbonate peak at 1790 cm$^{-1}$.

EXAMPLE 2

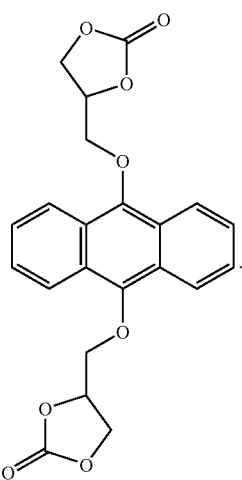 [SMILES: O=C1OCC(COc2c3ccccc3c(OCC3COC(=O)O3)c3ccccc23)O1]

12.05 g of 9,10-diglycidyl anthracene from IGM Resins BV. and 0.12 g of tetrabutylammonium bromide were mixed in a 0.5 liter Parr pressure reactor with a magnetic stirrer. The reactor was sealed and carbon dioxide gas was pressurised into the reactor to an initial pressure of approximately 350 psi at room temperature. The reactor was then heated to a temperature of approximately 150° C. The temperature/pressure profile was monitored throughout. When the temperature had been held constant at 150° C. and there appeared to be no further change in the pressure the reactor was cooled and the pressure released. The product was removed from the reactor.

Product yield 14.05 g of a light brown powder.

The product was analysed by IR, and showed a: very strong carbonate peak at 1781 cm$^{-1}$.

COMPARATIVE EXAMPLE 1

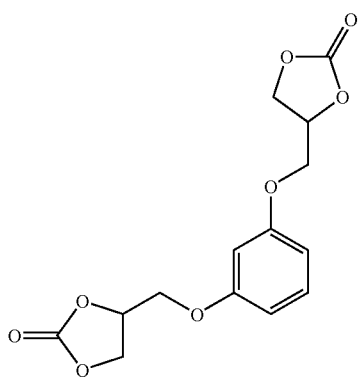 [SMILES: O=C1OCC(COc2cccc(OCC3COC(=O)O3)c2)O1]

50.64 g of resorcinol diglycidyl ether and 0.50 g of tetrabutyl ammonium bromide were mixed in a 0.5 liter Parr pressure reactor with a magnetic stirrer The reactor was sealed and carbon dioxide gas was pressurised into the reactor to an initial pressure of approximately 350 psi at room temperature. The reactor was then heated to a temperature of approximately 150° C. The temperature/pressure profile was monitored throughout. When the temperature had been held constant at 150° C. and there appeared to be no further change in the pressure, the reactor was cooled and the pressure released. The product was removed from the reactor.

Product yield 65 g of a glassy solid.

The product was analysed by IR and showed a very strong carbonate peak at 1793 cm$^{-1}$.

EXAMPLE 3

Varnish formulations were prepared based on

| | |
|---|---|
| Omnicat 440 photoinitiator ex IGM | 2.0% |
| Tegorad 2100 wetting aid ex TEGO | 0.1% |
| Sensitiser | 2% |
| UVACURE 1500 cycloaliphatic epoxide ex CYTEC | 95.9% |

A similar formulation was prepared but with no sensitiser and an additional 2% cycloaliphatic epoxide. All formulations were printed onto Lenetta charts using a No. 0 K bar and cured under a 300 W/inch medium pressure mercury arc lamp operating at half power. Prints were tested for their maximum line speed where a tack-free coating was obtained immediately after irradiation. The results are shown in Table 1.

TABLE 1

| Sensitiser example | Maximum tack-free line speed (m/min) |
| --- | --- |
| No sensitiser | 40 |
| Comparative Example 1 | 50 |
| Example 1 | >100 |
| Example 2* | >100 |
| 2-isopropylthioxanthone (ITX) | >100 |
| 9,10-dibutoxyanthracene | >100 |
| Irgacure 184 | >100 |
| Irgacure 2959 | >100 |

*formulation contains some insoluble material

These results demonstrate that the polycyclic sensitiser materials of the present invention can be used to significantly improve the cure speed of a cationic curing coating relative to formulations containing no sensitiser and are of equivalent performance to the well known commercial sensitisers ITX (obtained from IGM resins BV), dibutoxyanthracene (obtained from Kawasaki Kasei), Irgacure 184 and Irgacure 2959 (obtained from Ciba speciality chemicals).

EXAMPLE 4

A black ink formulation was prepared based on

| | |
| --- | --- |
| Omnicat 440 photoinitiator ex IGM | 2.0% |
| Special black 250 pigment | 15.0% |
| OXT 221 dioxetane monomer | 10.0% |
| Solsperse 32000 pigment dispersant | 1.25% |
| Sensitiser | 2% |
| UVACURE 1500 cycloaliphatic epoxide ex CYTEC | 69.75% |

A similar formulation was prepared but with no sensitiser and an additional 2% cycloaliphatic epoxide. All formulations were printed onto a white OPP plastic substrate using an "Easiproof" hand anilox coater and cured under a 300 W/inch medium pressure mercury arc lamp operating at half power. Prints were tested for their maximum line speed where a tack-free ink was obtained immediately after irradiation. The results are shown in Table 2.

TABLE 2

| Sensitiser example | Maximum tack-free line speed (m/min) |
| --- | --- |
| No sensitiser | 30 |
| Comparative Example 1 | <30 |
| Example 1 | 80 |
| 2-isopropylthioxanthone (ITX) | 100 |
| 9,10-dibutoxyanthracene | 80 |
| Irgacure 184 | 50 |
| Irgacure 2959 | 100 |

These results demonstrate the polycyclic sensitiser materials of the present invention can be used to significantly improve the cure speed of a cationic curing ink relative to formulations containing no sensitiser or using Irgacure 184, and are of equivalent performance to the well known commercial sensitiser dibutoxy anthracene (obtained from Kawasaki Kasei).

EXAMPLE 5

Varnish formulations were prepared based on

| | |
| --- | --- |
| Omnicat 440 photoinitiator ex IGM | 1.0% |
| Tegorad 2100 wetting aid ex TEGO | 0.1% |
| Example 1 | 0-20% |
| UVACURE 1500 cycloaliphatic epoxide ex CYTEC | Remainder of formulation |

All formulations were printed onto Lenetta charts using a No. 0 K bar and cured under a 300 W/inch medium pressure mercury arc lamp operating at half power. Prints were tested for their maximum line speed where a tack-free coating was obtained immediately after irradiation. The results are shown in Table 3.

TABLE 3

| % Example 1 | Maximum tack-free line speed (m/min) |
| --- | --- |
| 0 | 10 |
| 1 | 80 |
| 2 | 100 |
| 5 | >120 |
| 10 | >120 |
| 15 | >120 |
| 20 | >120 |

These results demonstrate the polycyclic sensitiser materials of the present invention, such as Example 1, can function within the formulation both as a sensitiser material and a reactive monomer. Non-reactive sensitisers such as dibutoxyanthracene are typically only used at levels of 1-2%. These results demonstrate that it is possible to use much higher levels of reactive sensitiser of the present invention, maintaining fast cure even at very low levels of the iodonium salt photoinitiator.

EXAMPLE 6

A white flexo ink was prepared based on;

| | |
| --- | --- |
| Titanium dioxide (FINNITITAN RDI/S ex Kemira) | 40.0% |
| UVACURE 1500 cycloaliphatic epoxide ex CYTEC | 40.3% |
| Propylene carbonate | 12% |
| Omnicat 440 photoinitiator ex IGM | 2% |
| Sensitiser | 2% |
| Solsperse 32000 pigment dispersant solution | 2.5% |
| Polyethylene wax | 1.2% |

A similar formulation was prepared but with no sensitiser and an additional 2% cycloaliphatic epoxide. All formulations were printed onto Lenetta charts using a No. 0 K bar and cured under a 300 W/inch medium pressure mercury arc lamp operating at half power. The maximum line speed for tack free cure was evaluated using the thumb twist test 5 seconds after UV exposure. The results are shown in Table 4.

TABLE 4

| Sensitiser | Max tack free cure speed m/min |
| --- | --- |
| None | 10 |
| Example 1 | 30 |
| Irgacure 184 | 30 |
| Irgacure 2959 | 50 |

The results demonstrate that cyclic carbonate sensitisers can be used to increase the cure speed of white flexo ink formulations. Since Example 1 of the present invention is neither coloured nor yellowing on cure it is also capable of being used easily in white inks where neither ITX nor dibutoxyanthracene are suitable due to yellowing issues.

The invention claimed is:

1. A composition comprising an iodonium salt cationic photoinitiator and a polycyclic aromatic compound having the formula (I):

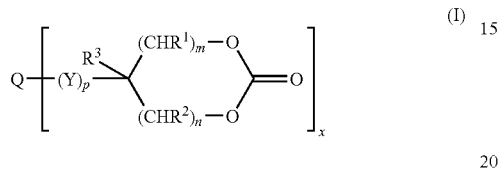

(I)

in which:
Q represents a residue of a polycyclic aromatic compound having at least two conjugated aromatic rings and having a valency x;
Y is an aliphatic carbon chain which may be interrupted by one or more oxygen atoms, sulphur atoms, phenylene groups, carbonyl groups, epoxide groups or linear or cyclic carbonate groups;
p is 0 or 1;
$R^1$ and $R^2$ are the same as or different from each other, and each represents a hydrogen atom, an alkyl group, a hydroxyalkyl group, an alkoxyalkyl group, an alkoxycarbonylalkyl group or a $C^2$-$C^5$ carbon chain which is attached to a carbon atom of Y to form a fused ring;
$R^1$ represents a hydrogen atom or an alkyl group; and
m and n are the same as or different from each other, and each is zero or a number from 1 to 4, provided that (m+n) is zero or a number from 1 to 4.

2. A composition according to claim 1, in which $R^3$ is H, Y is $Y^1$, p is 1, and x is 2 thereby having the formula (Ia):

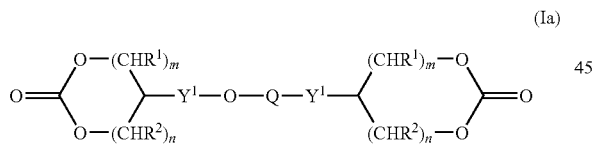

(Ia)

in which $Y^1$ represents an aliphatic group having from 1 to 3 carbon atoms.

3. A composition according to claim 2, in which $Y^1$ represents a methylene group.

4. A composition according to claim 1, in which the conjugated aromatic rings of Q are fused rings.

5. A composition according to 4, in which the conjugated aromatic ring is a naphthalene or anthracene ring system, which is substituted or unsubstituted.

6. A composition according to claim 1, in which: Q represents a residue of an anthracene or naphthalene ring system, which is unsubstituted or has at least one alkyl substituent; m+n=1; $R^1$, $R^2$ and $R^3$ all represent hydrogen atoms; Y is $Y^1$—O—; and $Y^1$ represents an alkylene group having from 1 to 3 carbon atoms.

7. A composition according to claim 2, in which: Q represents a residue of an anthracene or naphthalene ring system, which is unsubstituted or has at least one alkyl substituent; m+n=1; $R^1$ and $R^2$ both represent hydrogen atoms; and $Y^1$ represents an alkylene group having from 1 to 3 carbon atoms.

8. A composition according to claim 1, in which the conjugated aromatic ring is biphenyl.

9. A composition according to claim 1, in which the polycyclic aromatic compound is:

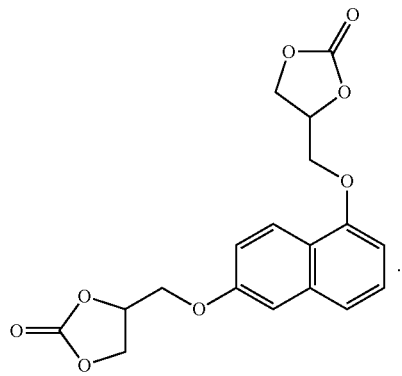 [SMILES: O=C1OCC(COc2ccc3c(OCC4COC(=O)O4)cccc3c2)O1]

10. A composition according to claim 1, in which the polycyclic aromatic compound is:

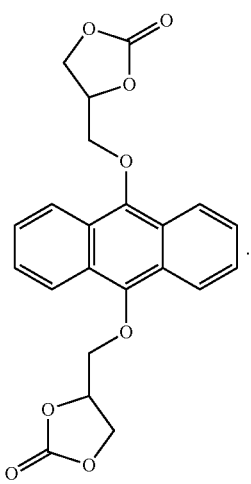 [SMILES: O=C1OCC(COc2c3ccccc3c(OCC3COC(=O)O3)c3ccccc23)O1]

11. A composition according to claim 1, further comprising a cationically polymerisable monomer or oligomer.

12. A composition according to claim 11, in which the polycyclic aromatic compound comprises from 1 to 50% by weight of the total polymerisable components of the composition.

13. A composition according to claim 11, in which the polycyclic aromatic compound comprises from 0.5 to 3% by weight of the total composition.

14. A composition according to claim 11, formulated as a coating composition.

15. A composition according to claim 11, formulated as a printing ink.

16. A composition according to claim 11, formulated as an inkjet ink.

17. A composition according to claim 11, formulated as an adhesive, release coating or primer.

18. A process for preparing a cured coating composition, which comprises applying a composition according to claim 11 to a substrate and exposing the coated substrate to curing radiation sufficient to cure the coating.

19. A process according to claim 18, in which the curing radiation is ultraviolet.

20. A composition according to claim 2 having the formula (Ia) in which $Y^1$ represents an alkylene group having from 1 to 3 carbon atoms.

\* \* \* \* \*